United States Patent

Montgomery et al.

[11] Patent Number: 5,358,522
[45] Date of Patent: Oct. 25, 1994

[54] THYROPLASTY IMPLANT

[75] Inventors: William W. Montgomery, Chestnut Hill; Stuart K. Montgomery, Needham, both of Mass.

[73] Assignee: Boston Medical Products, Inc., Waltham, Mass.

[21] Appl. No.: 93,259

[22] Filed: Jul. 16, 1993

Related U.S. Application Data

[62] Division of Ser. No. 707,704, May 30, 1991.

[51] Int. Cl.$^5$ .......................... A61F 2/02; A61F 2/20
[52] U.S. Cl. .......................................... 623/11; 623/9
[58] Field of Search ........................ 623/9, 10, 11, 12

[56] References Cited

U.S. PATENT DOCUMENTS

| D. 200,283 | 2/1965 | Gershen . |
| D. 284,507 | 7/1986 | Leopoldi . |
| 4,052,754 | 10/1977 | Homsy . |
| 4,094,303 | 6/1978 | Johnston . |
| 4,597,764 | 7/1986 | Black . |
| 4,744,792 | 5/1988 | Sander et al. . |
| 4,745,910 | 5/1988 | Day et al. . |
| 4,818,559 | 4/1989 | Hama et al. . |
| 4,938,234 | 7/1990 | Capriotti . |
| 5,061,280 | 10/1991 | Prescott . |
| 5,133,754 | 7/1992 | Laghi . |

FOREIGN PATENT DOCUMENTS

0453186A1 10/1991
WO91/09576 7/1991 PCT Int'l Appl. .

OTHER PUBLICATIONS

Isshiki, N. "Phonosurgery", Springer-Verlag, N.Y., pp. 77–104, 1989.
Sasaki, C. T. et al. "Longitudinol Voice Quality Changes Following Isshiki Thyropiasty Type I: The Yale Experience", Laryngoscope, vol. 100, pp. 849–852, 1990.
Maves, M. D. et al. "Phonosurgery:Indications and Pitfalls; Ann Otol Rhinol Laryngol", vol. 98, pp. 577–580, 1989.

*Primary Examiner*—Randall L. Green
*Assistant Examiner*—Elizabeth M. Burke
*Attorney, Agent, or Firm*—Fish & Richardson

[57] ABSTRACT

A thyroplasty implant having a tiered base for anchoring in a window cut through a thyroid lamina and a projecting member for causing medial displacement of a vocal cord. The tiered base has a bottom tier, a middle tier, and an upper tier, the bottom tier and upper tier being larger in area than the middle tier so as to facilitate anchoring the base in the window. The base is made of a firm biocompatible material to facilitate firm anchoring of the implant, and the projecting member being made of softer, biocompatible material that is sufficiently soft to avoid damage to the vocal cord. The projecting member is generally triangular in shape and has a portion that extends in a posterior direction from the base. A measuring tool having a projecting member of similar shape to that of the implant and a movable stop member is used to measure the optimum size implant.

7 Claims, 2 Drawing Sheets

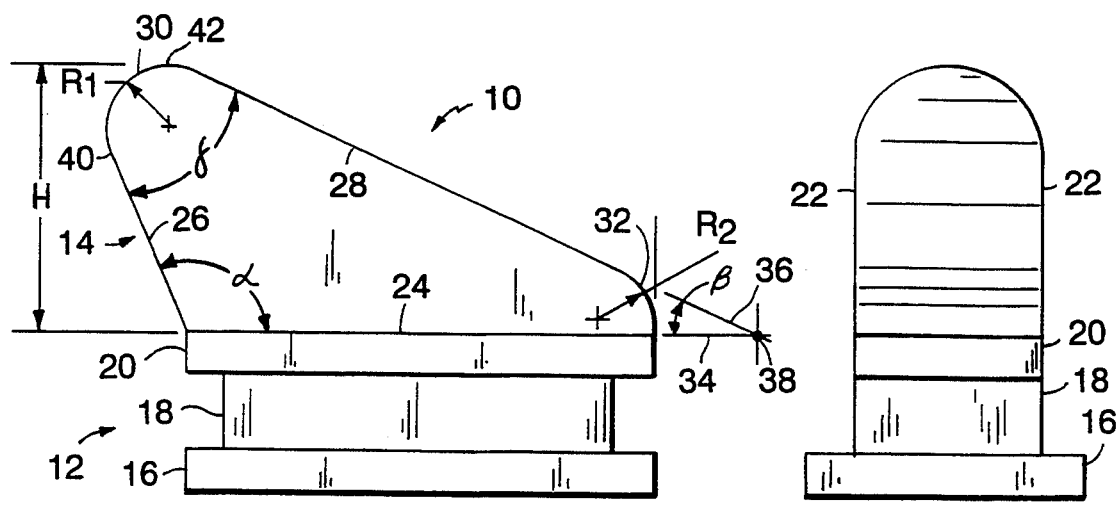
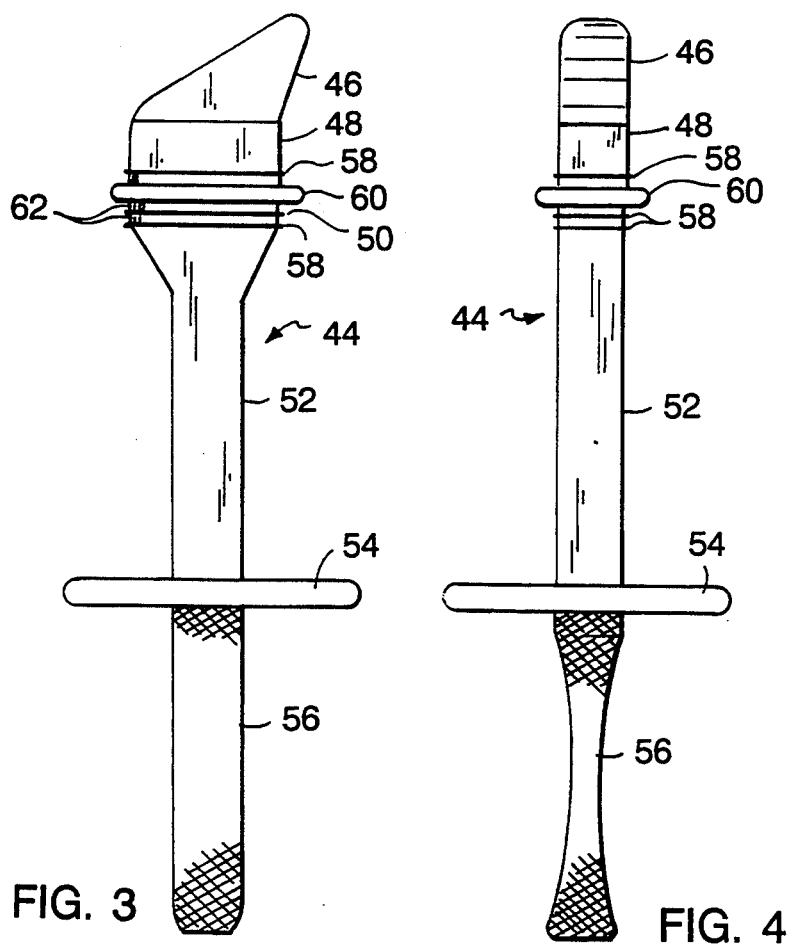

THYROPLASTY IMPLANT

This is a divisional of copending application Ser. No. 07/707,704, filed May 30, 1991 now allowed

FIELD OF THE OF THE INVENTION

The invention relates to a thyroplasty implant which is anchored in a window cut through a thyroid lamina and causes medial displacement of a vocal cord.

BACKGROUND OF THE INVENTION

When a patient's vocal cord has been paralyzed or is otherwise impaired, treatment can include medially displacing the nonfunctioning vocal cord to reduce the distance between it and the other, functioning vocal cord to improve voice and prevent aspiration. As is discussed in Isshiki, Nobuhiko, *phonosurgery*, (Springer-verlag, New York, 1989), pp. 77–104, the most common surgical technique to achieve this medial displacement is the cordal injection of Teflon. Another technique described in this reference is cutting a window in the thyroid lamina and medially displacing the cut window material (referred to therein as the "window") by implanting a shim or a plug in the resulting window (referred to herein to mean the opening cut through the thyroid lamina), the plug or shim having a projecting portion that extends inward beyond the window to displacing the cut window material, and thus the paralyzed vocal cord on the other side, toward the functioning vocal cord. One of the plugs described in Isshiki has a an angled projecting portion of varying height and a flange that is larger than the cut window and rests on the outside surface of the lamina. Another plug described in Isshiki has a projecting portion that has a posterior wedge extension that extends posteriorly beyond the window.

SUMMARY OF THE INVENTION

In one aspect, the invention features, in general, a thyroplasty implant having a tiered base with bottom and upper tiers that are larger in area than a window cut in the thyroid lamina and a middle tier that fits in the thyroid lamina. A projecting member extending from the upper tier causes medial displacement of a vocal cord. The triple-tiered approach facilitates firm anchoring of the implant at the desired location and orientation in the thyroid lamina.

In preferred embodiments the bottom tier extends beyond the middle tier around all sides, and the upper tier extends beyond the middle tier at only the anterior and posterior sides. The middle tier is about between 5 mm and 7 mm wide and about between 10 mm and 12 mm long. The projecting member has an inward dimension from the base to the innermost surface of about between 6 mm to 10 mm.

In another aspect, the invention features, in general, a two-piece thyroplasty implant having a base made of a firm biocompatible material (e.g., Shore A durometer between 50 and 90, most preferably about 70) to facilitate firm anchoring of the implant and a projecting member that is adapted to directly contact the vocal cord of softer, biocompatible material (e.g., Shore A durometer between 30 and 70, most preferably about 30, and in any event at least ten less than the projecting member) that is sufficiently soft to avoid damage to the vocal cord.

In another aspect, the invention features, in general, a thyroplasty implant having a projecting member that has two generally parallel side walls that extend inward from two sides of a cut window and are generally triangular in shape. The triangle has a first, base side that extends along a base of the implant and extends general parallel to the thyroid lamina when implanted, a second, rear side that extends posteriorly (when implanted) from the base side and makes an oblique angle with the base side, and a third, inner side that makes acute angles with the base side and the rear side. The innermost surface of the projecting member (between the inner sides of the triangles of the two side walls) is arcuate at its junctions with the side walls and with the rear surface between the rear sides of the triangle. The shape of the triangle permits medial displacement at a preferred location on the vocal cord (making desired contact with the vocal process of the arytenoid) at the same time as anchoring the base in a preferred location for cutting a window in the thyroid lamina, the latter location being offset from the former (preferably by about between 2 mm to 3 mm from the posterior side of the window to the posterior side of the projecting member). The arcuate surfaces are designed to facilitate desired direct contact and reduce potential trauma to the vocal cord.

In another aspect the invention features determining the optimum implant size by using a measuring tool having a projecting member of similar shape to that of the implant and a movable stop member that rests outside of the window. The stop member preferably is an elastomeric ring that is engaged between ridges on a calibrated portion of the tool.

Other advantages and features of the invention will be apparent from the following description of a preferred embodiment thereof and from the claims.

DESCRIPTION OF THE PREFERRED EMBODIMENT

The preferred embodiment will now be described.

DRAWINGS

FIG. 1 is an elevation of a thyroplasty implant according to the invention.

FIG. 2 is a side view of the FIG. 1 thyroplasty implant.

FIGS. 3 and 4 are side and end elevations of a tool used to determine what size implant should be used.

STRUCTURE

Figure 5:
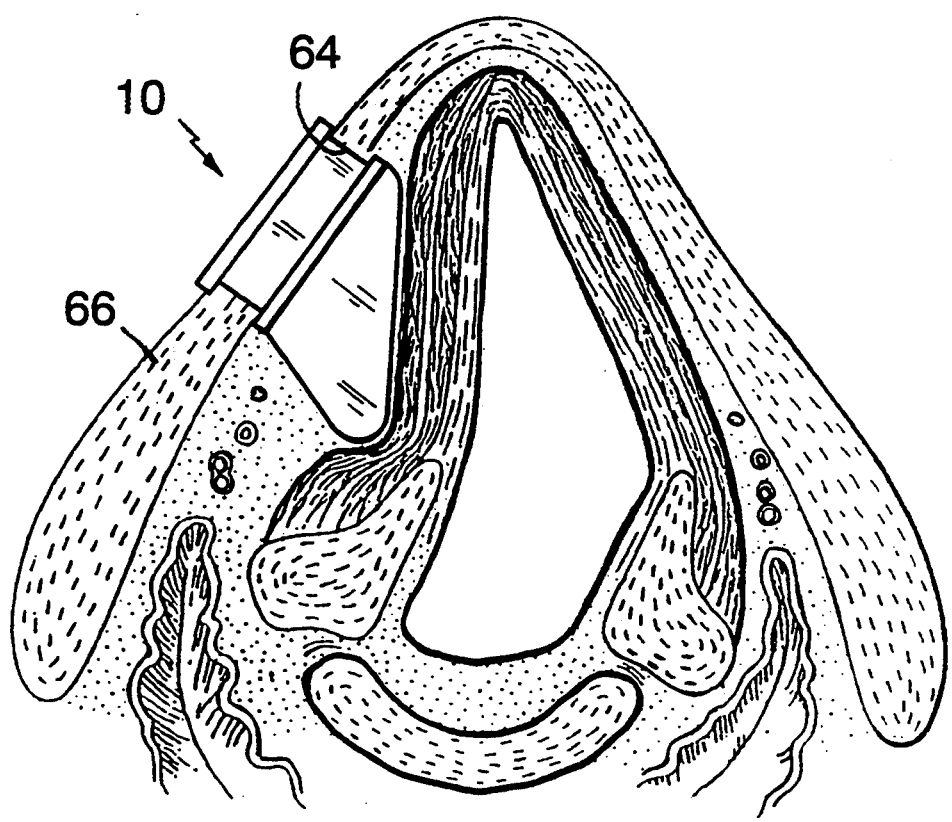
FIG. 5 is a diagrammatic, horizontal sectional view showing the FIG. 1 thyroplasty implant mounted in a window cut through a patient's thyroid lamina and medially displacing a vocal cord.

Referring to FIGS. 1 and 2, thyroplasty implant 10 has tiered base 12 and triangular projecting member 14. Implant 10 is made in four (or more) female sizes and in four (or more) male sizes. The female sizes have one size base 12, and the male sizes have a different size base 12, in order to accommodate the different sizes of female and male larynges. Within the female and male sizes, the triangular projecting members 14 have different heights, permitting the surgeon to select the height that will give the best results.

Base 12 has bottom tier 16 (1 mm thick), middle tier 18 (2 mm thick for female sizes and 3 mm thick for male sizes), and upper tier 20 (1 mm thick). In the female implants, bottom tier 16 is 12 mm long and 7 mm wide, middle tier 18 is 10 mm long and 5 mm wide, and upper tier 20 is 12 mm long and 5 mm wide. In the male implants, bottom tier 16 is 14 mm long and 9 mm wide, middle tier 18 is 12 mm long and 7 mm wide, and upper tier 20 is 14 mm long and 7 mm wide.

Projecting member 14 has the same width and length at its bottom as the upper tier 20 below it. Projecting member 14 has two generally parallel side surfaces 22 that are generally triangular in shape. The triangle has a first, base side 24 that extends along upper tier 20 of base 12 of the implant, a second, rear side 26 that extends posteriorly (when implanted) from base side 24 and makes an oblique angle $\alpha$ with base side 24, and a third, upper side 28 that makes acute angle $\beta$ with the base side 24 and acute angle $\gamma$ with rear side 26. Side walls 22 curve toward each other at upper side 28 at a radius that is equal to one-half of its width, so that the uppermost surface of projecting member 14 is arcuate. The junction 30 between the second and third sides 26, 28 on all sizes has a radius of curvature $R_1$ of 1.59 mm, and the junction 32 between the first and third sides 24, 28 on all sizes has a radius of curvature $R_2$ of 1.4 mm. Axis 34 along first side 24 intersects axis 36 along third side 28 at a point 38 that is 2.5 mm beyond upper tier 20 in the female sizes and 3.5 mm beyond upper tier 20 in the male sizes. The rearmost portion 40 of projecting member 14 is 2 mm behind upper tier 20 in the female sizes and 3 mm behind upper tier 20 in the male sizes; this offset permits contact with the vocal process of the arytenoid at the same time as anchoring the base in a preferred location for cutting a window in the thyroid lamina. The arcuate surfaces are designed to facilitate desired direct contact and reduce potential trauma to the vocal cord. The heights H of the uppermost portions 42 of projecting member 14 above upper tier 20 are 6 mm, 7 mm, 8 mm and 9 mm for the female sizes, and 8 mm, 9 mm, 10 mm and 11 mm for the male sizes.

Implant 10 is made of biocompatible materials, in particular two medical grade silicone or thermoplastic elastomer polymers of different durometer (available from Dow Corning Midland, Mich. under the Silastic trade designation and Concept Polymers, Clearwater, Fla. under the C-Flex trade designation, respectively). Base 12 is made of high durometer (approximately 70 durometer Shore A) material in order to be sufficiently firm to provide secure anchoring in the thyroid lamina. Projecting member 14 is made of low durometer material (approximately 30 durometer Shore A) in order to be sufficiently soft to avoid damage to the vocal cord. Implant 10 is made by insert molding, first molding one piece, and then placing it in the mold for the other piece.

Referring to FIGS. 3 and 4, there is shown tool 44 for use in determining which size implant should be used. Going from top to bottom, tool 44 has triangular projecting member 46, extension 48, calibrated attachment portion 50, shaft 52, base 54, and knurled handle 56. Two sizes are provided for tool 40, one size for use with women, and another size for use with men. Extension 48 has a rectangular cross-section the same size as middle tier 18 of implant 10. Triangular projecting member 40 is of the same material as and is generally of the same shape as projecting member 14 of implant 10. Calibrated portion 50 has ridges 58 spaced 1 mm apart (center to center) adapted to receive resilient ring 60 at different locations corresponding to different heights H for implant 10. Indicia 62 between adjacent ridges 58 indicate the height H for implant 10 that functions similarly to tool 40 when ring 60 is in the indicated position.

Use

The surgical procedure for implanting thyroplasty implant 10 is performed under local anesthesia. After surgical exposure of the larynx, window 64 is created in thyroid lamina 66 by cutting a rectangular section of cartilage using either a surgical blade or surgical saw. The dimensions of window 64 are 5 mm by 10 mm for females and 7 mm by 12 mm for males. The anterior edge of window 64 is located a distance laterally from the anterior midline of the thyroid cartilage of 5 mm in the female and of 7 mm in the male. The perichondrium is elevated underneath the cartilage window, and the cut portion of cartilage is carefully removed from the window. The perichondrium is elevated in all directions underneath the window. An anterior anteroposterior line of cautery is made in the perichondrium along the length of the mid portion of the window. An incision of the perichondrium is carefully accomplished without touching the underlying muscle fibers.

Tool 44 is then used to determine which size implant 10 should be selected, with ring 60 initially in the position corresponding to the shortest height implant. Triangular projecting member 46 is introduced through window 64 until ring 60 rests against outer surface 68 of the thyroid lamina. The patient is asked to phonate to see if there is a good improvement in his or her voice, and a fiberoptic laryngoscope is inserted into the area above the larynx to see if the vocal cord has been medialized to a point where the vocal cords touch during phonation. If the optimum voice has not been achieved, and the vocal cords need to be moved more medially, tool 44 is removed, and ring 60 is moved to the next groove position on calibrated portion 50. Triangular projecting member 46 is introduced through window 64 and the voice is analyzed and the cords examined, and so on until the optimum size implant has been determined.

The physician then selects the optimum size implant 10. Obtuse triangular projecting member 14 of implant 10 is first introduced through the window in the thyroid lamina, the overhanging portion at the junction of sides 26, 28 being posterior. Upper tier 20 of base 12 is also inserted in the window, using a curved instrument inserted between the top and bottom tiers of the base of the implant, and implant 10 snaps into place. Upper tier 20 becomes an internal flange that helps prevent displacement of implant 10. Middle tier 18 of base 12 remains in thyroid lamina window 64. Bottom tier 16 of base 12 acts as an external flange to help prevent implant 10 from moving through thyroid lamina window. The perichondrium is sutured over the implant to further enhance its stability, and the incision is repaired. Once the implant has been inserted, the chance of medial and lateral displacement is remote, as is migration of the implant. If the implant requires changing either at the time of surgery of during a secondary procedure, the posterior end of the implant is grasped with forceps or a mosquito hemostat. With outward pressure, the implant snaps out easily without damaging either cartilaginous or soft tissue structures. Because of uniformity of base design, different size implants can be reinserted with no change in the thyroid cartilage window.

Implant 10 has application for treatment for unilateral vocal cord paralysis, after a hemilaryngectomy, following laryngeal trauma when vocal cords do not approximate, for treatment of bowed vocal cords, and for treatment of vocal cord atrophy. The use of a plurality of sizes and measuring instrument 44 guarantees that the optimum size is employed for the patient. It also avoids the need to fashion or alter the implant at time of surgery.

Other embodiments of the invention are within the scope of the appended claims.

What is claimed is:

1. A thyroplasty implant for anchoring in a window cut through a thyroid lamina and causing medial displacement of a vocal cord comprising a base for anchoring in said window, said base including a first tier to be received in said window, said first tier having a length and width, said first tier being larger in size along said length and width than said first tier is thick along a perpendicular axis, and a projecting member attached to and extending from said base along said perpendicular axis for causing medial displacement of a vocal cord, said base being made of a firm biocompatible material to facilitate firm anchoring of the implant, said projecting member being made of biocompatible material that is softer than said firm biocompatible material and is sufficiently soft to avoid damage to the vocal cord.

2. The implant of claim 1 wherein said base is made of material having a first Shore A durometer between 50 and 90, and said projecting member is made of material having a second Shore A durometer between 30 and 70, and said first Shore A durometer is at least ten greater than said second Shore A durometer.

3. The implant of claim 2 wherein said second Shore A durometer is between 30 and 50, and said first Shore A durometer is between 50 and 90.

4. The implant of claim 3 wherein said second Shore A durometer is between 30 and 40, and said first Shore A durometer is between 60 and 80.

5. The implant of claim 1 wherein said middle tier is about between 5 mm and 7 mm wide and about between 10 mm and 12 mm long.

6. The implant of claim 1 wherein said first tier is a middle tier and said base also has a bottom tier, and an upper tier, said bottom tier and said upper tier being larger in area than said middle tier so as to facilitate anchoring of said base in said window, said window having an area that is less than the areas of said bottom and upper tiers, said middle tier being smaller in thickness along an axis from said bottom tier to said upper tier than the size of said middle tier along a perpendicular axis, said bottom tier, middle tier, and upper tier having respective lengths and widths that are aligned.

7. The implant of claim 6 wherein said middle tier is about between 5 mm and 7 m wide and about between 10 mm and 12 mm long.

* * * * *